United States Patent
Bermudez Castel et al.

(10) Patent No.: US 10,441,427 B2
(45) Date of Patent: Oct. 15, 2019

(54) ARTIFICIAL JOINT

(71) Applicants: INNOVATIVE MINDS S.L, Terrassa, Barcelona (ES); Adrián Bermudez Castel, Terrassa (ES); Lluís Font Vizcarra, Terrassa (ES)

(72) Inventors: Adrián Bermudez Castel, Terrassa (ES); Lluís Font Vizcarra, Terrassa (ES)

( * ) Notice: Subject to any disclaimer, the term of this patent is extended or adjusted under 35 U.S.C. 154(b) by 18 days.

(21) Appl. No.: 15/537,374

(22) PCT Filed: Dec. 17, 2015

(86) PCT No.: PCT/EP2015/080248
§ 371 (c)(1),
(2) Date: Jun. 16, 2017

(87) PCT Pub. No.: WO2016/097160
PCT Pub. Date: Jun. 23, 2016

(65) Prior Publication Data
US 2018/0000599 A1 Jan. 4, 2018

(30) Foreign Application Priority Data

Dec. 18, 2014 (EP) .................................... 14382536
Dec. 19, 2014 (EP) .................................... 14382539

(51) Int. Cl.
*A61F 2/38* (2006.01)
*A61F 2/30* (2006.01)
(Continued)

(52) U.S. Cl.
CPC .................. *A61F 2/38* (2013.01); *A61F 2/30* (2013.01); *A61N 1/05* (2013.01); *A61N 1/205* (2013.01);
(Continued)

(58) Field of Classification Search
CPC ....................................................... A61F 2/38
See application file for complete search history.

(56) References Cited

U.S. PATENT DOCUMENTS

| | | |
|---|---|---|
| 2005/0228503 A1 | 10/2005 | Gundolf |
| 2008/0133016 A1 | 6/2008 | Heinz |
| 2010/0204551 A1 | 8/2010 | Roche |

FOREIGN PATENT DOCUMENTS

| | | |
|---|---|---|
| DE | 2020080015661 U1 | 5/2009 |
| EP | 0 346 058 B1 | 12/1993 |
| WO | 2014145491 A | 9/2014 |

*Primary Examiner* — Matthew W Schall
(74) *Attorney, Agent, or Firm* — Seed IP Law Group LLP

(57) ABSTRACT

The present invention relates to an artificial joint comprising a first joint portion (101), a second joint portion (105) and an intermediate portion (103). The first joint portion and the second joint portion each comprise an electrically conductive material and the intermediate portion comprises a non-conductive material and is arranged in between the first joint portion and the second joint portion such that the first joint portion is electrically isolated from the second joint portion. The artificial joint further comprises an internal electronic unit (110) provided inside of the isolating portion being connected to the first joint portion via at least one first electrode (111) and to the second joint portion via at least one second electrode (113). Thus, a first voltage can be applied to the first joint portion and a second electric voltage can be applied to the second joint portion, the voltages being with reference to a common reference potential.

20 Claims, 4 Drawing Sheets

(51) Int. Cl.
  *A61N 1/20* (2006.01)
  *A61N 1/05* (2006.01)
  *A61F 2/28* (2006.01)
  *A61F 2/46* (2006.01)
  *A61B 5/00* (2006.01)
(52) U.S. Cl.
  CPC ..... *A61B 5/4528* (2013.01); *A61F 2002/2821* (2013.01); *A61F 2002/469* (2013.01)

ARTIFICIAL JOINT

1. FIELD OF THE INVENTION

The present invention relates to an artificial joint adapted to prevent bacterial adherence by the application of suitable electric fields.

2. TECHNICAL BACKGROUND

Bacterial infection can lead to undesirable complications in particular during and directly after implanting an implantable device such as an artificial joint, i.e. an artificial knee, a hip prosthesis, a spinal implant or the like. Such infections usually are the result of contamination of implant surfaces due to adherence of bacteria and/or formation of biofilms. Once such contamination is present, up to now infection treatments usually require the use of antibiotics for example locally at the implant.

Even though the majority of developments addressing such problems are based on chemical approaches, developments exist making use of the application of electric fields. A typical prior art example is disclosed in document EP 0 346 058 B1. Therein a catheter is described including electrodes for applying electric fields across the catheter surfaces in order to reduce bacterial attachment. Therein, in particular the application of predominantly negative electrical fields is suggested.

Developments exist which focus on combining the effect of electrical fields with the use of medicine such as antibiotics. A typical prior art example is described in Document US 2010/0204551 A1. This document discloses an artificial knee implant wherein sensors including electrodes are provided at first and second joint portions, i.e. at femoral and tibial portions. Using the sensors connected to an external control device such as a personal computer, an infection can be detected and reported for example to a doctor. Once the infection is detected, according to this document it is suggested to apply local electric fields at a strength in between 0.2 kV/cm and 20 kV/cm to the electrodes for inducing electroporation of the bacterial cells. Due to the resulting increase of permeability of the cell membrane penetration of antibiotics, cytokines or other medicines is facilitated.

It is an object of the present invention to improve the state of the art by providing an artificial joint which allows prevention of infections and bacterial contamination of the implant surfaces. A further object is the provision of an artificial joint which allows reduction of bacterial adhesion to surfaces of the artificial joint and prevents the formation of biofilms, preferably before an infection is present. It is a further object of the present invention to provide an artificial joint which allows prevention of infections without the need for the use of medicine such as antibiotics. It is an even further object of the present invention to provide an artificial joint which allows prevention of infections while avoiding the use of large electric fields.

These and other objects which will become apparent upon reading the following description are solved by an artificial joint according to claim 1 and a system according to claim 15.

3. SUMMARY OF THE INVENTION

According to the invention an artificial joint is provided comprising a first joint portion, a second joint portion and an intermediate portion which are mechanically connected such that the first joint portion is movable with respect to the second joint portion. For example, in the case of an artificial knee, the first joint portion can be a femoral implant and the second joint portion can be a tibial implant while the intermediate portion can be a polyethylene insert in between the implants. As it will be clear for the skilled person, in this case the first joint portion is movable with respect to the second joint portion as the femoral implant can be pivoted with respect to the tibial implant. Preferably, the first joint portion, the second joint portion and the intermediate portion essentially form the artificial joint. In other words, preferably the artificial joint consists of the first joint portion, the second joint portion and the intermediate portion.

Thereby, the first joint portion and the second joint portion comprise a conductive material and the intermediate portion comprises a non-conductive material and is arranged in between the first joint portion and the second joint portion such that the first joint portion is electrically isolated from the second joint portion. Preferably, at least the outer surfaces of the first joint portion and the second joint portion are electrically conductive. Further, preferably the first and second joint portions are formed from a conductive material. In a preferred embodiment, the conductive material is a metal such as a lightweight metal as used in the art. Preferably, the intermediate component is formed from a plastic material such as polyethylene. In a further preferred embodiment, the artificial joint is an artificial knee, the first joint portion is a femoral implant and the second joint portion is a tibial implant.

According to the invention, the artificial joint further comprises an internal electronic unit which is provided inside of the isolating portion and is connected to the first joint portion via at least one first electrode and to the second joint portion via at least one second electrode such that a first electrical voltage can be applied to the first joint portion and a second electric voltage can be applied to the second joint portion. In other words, the intermediate portion preferably houses the internal electronic unit allowing for connections such as electrical connections to extend through corresponding portions of the intermediate portion towards the outside.

Thereby, the first electrical voltage and the second electrical voltage are applied with reference to a common reference potential. For example, both the first electrical voltage and the second electrical voltage can be applied with reference to a common ground potential. Similarly, the reference potential can be the same potential as the potential of the second joint portion, preferably the tibial portion. Alternatively, also a potential of the first joint portion can be used as common reference potential.

Thus, as opposed to conventional prior art solutions, the artificial joint according to the invention is provided with an internal electronic unit inside of an isolating portion such as a polyethylene insert of an artificial knee. Only necessary connections need to extend from the inside of the intermediate portion towards the outside thus providing a simple non-complex construction whereby none of the potentially fragile electronic components need to be exposed to the outside for example to synovial fluid which may cause defects for example due to corrosion of components when the implantable device, i.e. the artificial joint, is to be inside of the human body for a long time or even forever. In other words, the simple and non-complex construction offered by the present invention allows for the provision of an artificial joint including electronics allowing for a particularly high lifetime. This is of particular advantage in the present field since for example further surgeries are prevented which may otherwise become necessary in order to remove defective components.

In a preferred embodiment, the internal electronic unit is adapted to apply the first electrical voltage and the second electrical voltage at opposing polarities and is adapted to allow the first and second electrical voltages to be applied as AC, i.e. alternating current, voltage or as DC, i.e. direct current, voltage. It was surprisingly found that when voltages are applied in this way, independently of the respective polarity, a reduction in bacterial adhesion to the corresponding surfaces was achieved. Both in the case of negatively charged surfaces and positively charged surfaces it was possible to efficiently repel bacteria.

The present inventors experimentally determined that by applying an appropriate DC voltage to conductive surfaces, a reduction of bacterial surface contamination of 90% could be achieved. By applying a 200 Hz pulsed electric filed resulting in 2.5 μs pulses of 4 A, a reduction of 95% in bacteria adhering to respective surfaces could be achieved. In the same experiments, the inventors determined that essentially the same results were achieved independently of the polarity of the charge of the surfaces. Even though in theory, it was expected that bacterial adherence on negatively charged surfaces should be lower, the present inventors found experimentally that at least no significant difference can be observed depending on the polarity. Thus, in the case for example of an artificial knee, the first electrical voltage can be applied to the femoral implant and the second electrical voltage can be applied to the tibial implant so that the resulting electrical field points from one of the implants towards the other of the implants in order to achieve a repelling effect preventing the adhesion of bacteria to the implant surfaces.

In a preferred embodiment, the first electrode is attached to an outer surface of the intermediate portion, arranged essentially parallel to said outer surface in between the intermediate portion and the first joint portion in electrical contact with a corresponding contact surface of the first joint portion. Thus, an electrical connection can be established between the first joint portion and the internal electronic unit inside of the intermediate portion. In other words, the first electrode may be fixedly attached to the intermediate portion which preferably in turn is fixedly attached to the second joint portion. At the same time, while the first electrode is in electrical contact with the first joint portion it is not fixedly attached to said first joint portion but allows for a movement as necessary. Thus, the first electrode is preferably shaped and arranged in between the intermediate portion and the first joint portion to allow for reduced movement upon moving of the second joint portion with respect to the first joint portion. For example, the first electrode may be of a suitable soft metal or conductive plastic material with a suitably polished surface.

In a preferred embodiment, the artificial joint further comprises a central electrode provided in between the first joint portion and the second joint portion, whereby the internal electronic unit is adapted to apply a third electrical voltage to the central electrode. The third electrical voltage is applied with reference to the common reference potential. In other words, the third electrical voltage is applied with reference to the same reference potential as are the first and the second electrical voltage. Even though no strong dependence of the repelling effect on the polarity of the first and second joint portions was found, the provision of the central electrode allows fine-tuning the electric field distribution across the artificial joint in a desirable way depending on the respective geometry of the artificial joint.

For example the central electrode could be used as bait for attracting bacteria while keeping them away from the first and second joint portions. The provision of a third electrode thus provides the possibility of applying a variety of combinations of polarities as well as a variety of voltage strengths to the respective electrodes to efficiently fine-tune the electric field distribution and fine-tune the same with respect to the individual geometry of the used artificial joint. Preferably, the central electrode is provided within an outer surface of the intermediate portion in electrical contact with synovial fluid. This construction allows for the particular advantage to electrically contact also the synovial fluid which further attributes to fine tuning the electrical field distribution and preferably also enhances the bait effect of the central electrode.

Preferably, the first and second electrical voltages are applied such that the first joint portion and the second joint portion are set to a voltage of the same polarity and the third electrical voltage is applied such that the central electrode is set to the opposing polarity. For example, the first and second electrical voltages can be set at a positive polarity while the central electrode is set to a negative polarity. Preferably, the first and second electrical voltages are applied at the same voltage value at the same polarity. It was found that in this way, an advantageous repelling effect can be achieved and the bacteria adhesion to the surfaces of the first and second joint portions can beneficially be prevented.

In a preferred embodiment, the internal electronic unit is adapted to communicate with an external control device, the external control device thus being adapted to control an application of the first electrical voltage and the second electrical voltage. Preferably, the external control device is further adapted to control the third electrical voltage. Preferably, the external control device is adapted to control an application of the first electrical voltage and the second electrical voltage when the artificial joint is implanted within a patient body and the external control device is placed outside of the patient body.

In other words, the application of the voltages can be controlled, i.e. for example the strengths of the voltages as well as the respective polarities can be controlled from the outside. To this end, the intermediate portion can preferably be provided with a socket electrically connected to the internal electronic unit and the external control device can be provided with a cable connectable to said socket.

In a preferred embodiment, the internal electronic unit is adapted to apply the first and the second electrical voltage such that a resulting electrical field strength is in between V/cm and 60 V/cm, preferably in between 0 V/cm and 55 V/cm, more preferably in between 0 V/cm and 40 V/cm, yet even more preferably in between 0 V/cm and 20 V/cm, and most preferably in between 10 V/cm and 20 V/cm.

It was found by the present inventors that by applying voltages within this range, for example for a typical artificial knee bacterial adhesion is expected to be significantly reduced even though the field strength may not be sufficient for killing bacteria. The inventors observed that by the application of a voltage in order to create an electric field in particular within the most preferred range in between 10 V/cm and 20 V/cm, a resulting current flowing due to the surrounding fluid environment is sufficient for an advantageous repelling effect. At the same time, the resulting electric fields are not localized electric fields of high field strength which may have detrimental effects on components of the artificial joint or the surrounding synovial fluid. It is further possible to repel bacteria preventing adhesion and thus preventing infections without the use of medicine such as antibiotics.

Thus, by applying voltages in the range suggested above, the inventive construction of the artificial joint allows for an advantageous repelling effect which enables efficient prevention of infections. However, as the skilled person will understand, by appropriately changing the voltages, it also is possible to treat an infection by disrupting or releasing an existing biofilm with the inventive artificial joint.

In a preferred embodiment, a pair of the first joint portion, the second joint portion and the central electrode is set to essentially the same voltage and the voltage difference is a voltage difference between said pair and the remaining one of the first joint portion, the second joint portion and the central electrode. For example, the first joint portion and the second joint portion can be set to essentially the same voltage while the central electrode is set to a different voltage, the resulting voltage difference being as described above. In this way, the central electrode may act as bait for attracting bacteria in order to keep the first and second joint portion free of bacteria.

In a preferred embodiment, when the first electrical voltage is applied to the first joint portion and the second electrical voltage is applied to the second joint portion, the first joint portion and the second joint portion are charged accordingly and a resulting electrical field is generally oriented from one of the first joint portion and the second joint portion to the other one of the first joint portion and the second joint portion. This construction allows that local electric fields of high strengths are avoided which may have locally disadvantageous effects. High strength fields may cause large current flow which in turn may result in undesirable local temperature rises or the like. At the same time, it is expected that the global charge of the first joint portion and the second joint portion, i.e. of the respective surfaces thereof, are sufficient to efficiently repel bacteria and prevent adhesion of the same.

In a preferred embodiment, the internal electronic unit is further provided with a transceiver and the external control device is provided with a transmitter such that the external control device is adapted to wirelessly control an application of the first electrical voltage and the second electrical voltage. The transceiver provided within the internal electronic unit is adapted to receive and transmit data from and to the transmitter of the external control device. Data communicated between transceiver of the internal electronic unit and the transmitter of the external control device 200 can e.g. data acquired from sensors connected to the internal electronic unit such as temperature or pH values or the like. Data communicated between said transceiver and said transmitter may further include control data sent from the transmitter to the transceiver in order to control application of voltages, i.e. voltage strengths and/or voltage frequencies in the case of AC voltages. Even though referred to as transmitter herein to be distinguishable from the transceiver of the internal control unit, the transmitter of the external control device is adapted to send data to the transceiver of the internal control unit and in turn also to receive data from the transceiver of the internal control unit. By this arrangement it becomes advantageously possible to avoid the need of cables and the like such that it is possible to connect and reconnect to the device without any further surgery being necessary.

Preferably, the external control device and the internal electronic unit are adapted such that electrical power necessary for applying the first and second electrical voltage is provided from the external control device to the internal electronic unit. It becomes thereby possible to avoid the need for a battery inside of the implanted device which is on the one hand beneficial since disadvantageous effects of batteries are avoided. At the same time, it is possible to reconnect and use the internal device even after the artificial joint may be already implanted for a long time.

In a preferred embodiment, the artificial knee further comprises a receiver coil provided within, preferably embedded within, the intermediate portion in electrical connection with the internal electronic unit, and the external control device is provided with a transmitter coil such that electrical power necessary for applying the voltages, i.e. the first and the second electrical voltage and preferably the third electrical voltage, can be provided from the external control device to the internal electronic unit through the receiver coil and the transmitter coil by inductive power transmission. By the provision of these features, it becomes advantageously possible to reconnect to the internal electronic unit without the use of cables such that also when the artificial joint is implanted for a long time, reconnection is possible without any further surgery. Preferably, the receiver coil is provided embedded within an outer portion of the intermediate portion surrounding the internal electronic unit. This advantageous construction allows for example to place a relatively large coil within the intermediate portion being protected from the outside, i.e. being protected for example from effects such as corrosion which may be caused by contact with synovial fluid.

In a preferred embodiment, the transceiver of the internal control unit can be the same entity as the receiver coil. In other words, the functions of the transceiver can be realized by the receiver coil, thus advantageously realizing both functions of data communication with the external control device and power reception from the external control device within one and the same entity.

In a preferred embodiment, the internal electronic unit is further provided with at least one sensor which is provided in communication with the environment of the artificial joint and thus adapted to detect at least one of temperature of the synovial fluid, conductivity of the synovial fluid, pH of the synovial fluid or a marker of cell death within the synovial fluid. There are several ions, enzymes and biomarkers related with inflammation (C-reactive protein, creatinine-kinase), cellular destruction (K concentrations) and bone resorption (RANKL concentrations) which may be detected by appropriate biochemical sensors.

The present inventors found that it is in particular desirable to avoid detrimental effects to the patient body which may arise due to the application of electric fields. For example, electric field and in particular localized electric fields of high strengths can cause electrolysis of water. In combination with substances e.g. present within the synovial fluid such electrolysis can cause formation for example of ions and substances toxic to the human body. Also molecular vibrations can be caused resulting for example in undesirable temperature increases. Therefore, it is advantageous if on the one hand voltage application can be controlled from the outside. At the same time, it is advantageous if such detrimental effects can be detected. To this end, according to the preferred embodiments, sensors are provided to detect such effects.

In a preferred embodiment, the internal electronic unit is adapted to communicate a signal received from the at least one sensor to the external control device and the external control device is adapted to automatically adjust the first electrical voltage applied to the first conductive component and the second electrical voltage applied to the second conductive component in response to the sensor signals. Thus, preferably a feedback loop is provided which allows automatically controlling the application of voltages in response to at least one sensor signal in order to avoid detrimental effects on body portions surrounding the artificial joint. Thus, even though a patient or a doctor may not be aware of for example an undesirable temperature change even though communicated to an outside controller, the provision of the automized feedback loop helps to avoid such detrimental effects. For example if it is detected that the pH value of the synovial fluid increases or that the temperature increases, voltages can be decreased to decrease such effects or even turned off.

In a preferred embodiment, the artificial joint is a knee prosthesis, the first joint portion is a femoral portion, the second joint portion is a tibial portion and the intermediate portion is a polyethylene insert provided in between the femoral portion and the tibial portion.

According to the invention, further a system is provided comprising the artificial joint as defined by any of the embodiments above and the external control device.

Further, according to the invention, a use of the artificial joint as described in any one of the above embodiments is provided for therapy, preferably for preventing adhesion of bacteria when the artificial joint is implanted. In addition and as already stated above, by appropriately changing the voltages, it also is possible to treat an infection and destroy an existing biofilm with the inventive artificial joint. Consequently, a further use of the artificial joint as described in any one of the above embodiments is provided for treating an infection and disrupting or releasing an existing biofilm with the inventive artificial joint.

4. DESCRIPTION OF THE PREFERRED EMBODIMENTS

In the following, the invention is described exemplarily with reference to the enclosed figures in which.

Even though the following embodiments are described using the example of an artificial knee, the skilled person will understand that the invention is applicable also to a different prosthesis such as to artificial hips, shoulders, a spine prosthesis, or the like.

Figure 1:
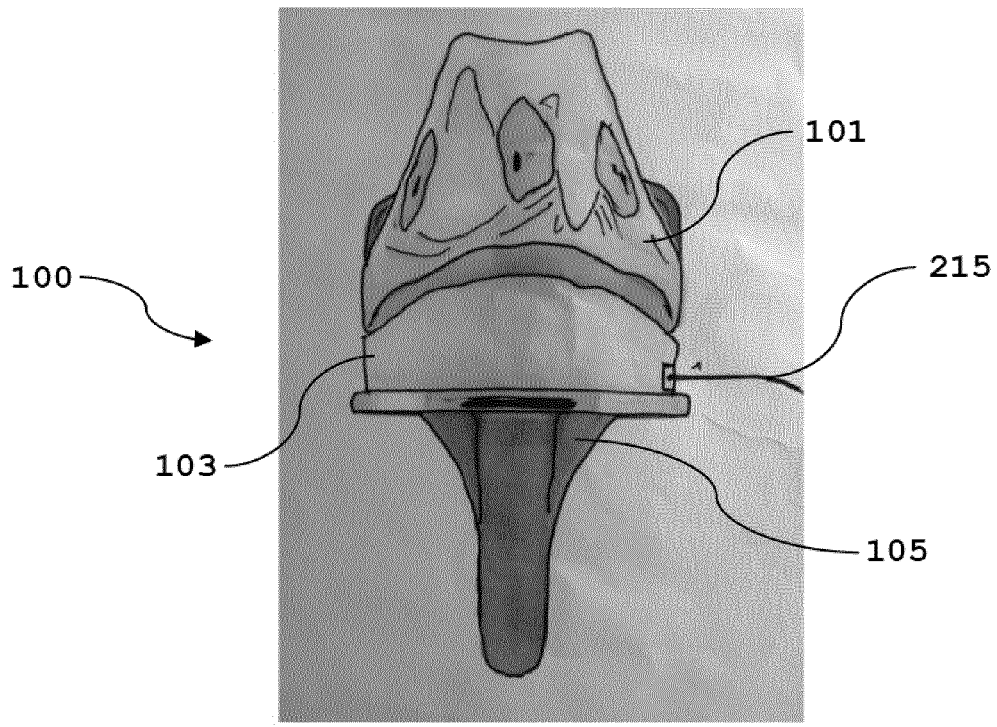
FIG. 1 shows a schematic view of an artificial joint.

FIG. 1 shows a schematic illustration of an artificial knee 100 which is an example of an artificial joint. As shown in the figure, the artificial knee 100 comprises a first joint portion 101 which in the shown case is a femoral portion 101, an intermediate portion 103 and a second joint portion 105 which in the shown case is a tibial portion 105. The intermediate portion 103 is formed of a non-conductive material such as a suitable plastic material as for example polyethylene and comprises a socket to which a cable 215 is attached connecting an internal electronic unit (not shown in this figure) to an external control device (also not shown).

Figure 2:
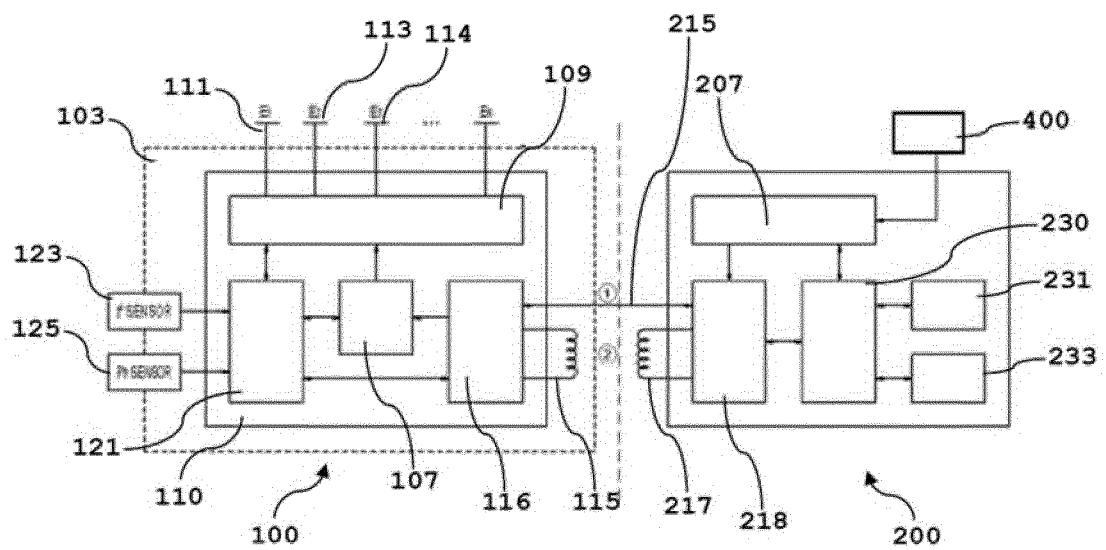
FIG. 2 is a schematic illustration of the internal electronic unit and the external control device.

FIG. 2 illustrates an example of a system comprising the artificial joint 100 and the external control device 200. As shown, the artificial joint 100 includes the intermediate portion 103 which houses the internal electronic unit 110. The internal electronic unit 110 is a unit, e.g. a small box, which in turn houses the electronic parts necessary for the electronic functions of the artificial joint 100. As shown, the internal electronic unit 110 is provided with a plurality of electrodes, in particular the first electrode 111, the second electrode 113 and the central electrode 114. If necessary, more electrodes may be provided which is illustrated by the electrode $E_N$ and all of the electrodes are connected to an electrode controller 109. Further, the internal electronic unit 110 is provided with sensors, in particular with a temperature sensor 123 and a pH sensor 125 which are controlled by a sensor controller 121. The internal electronic unit 110 is further provided with a transceiver 115 which in the shown case coincides with a receiver coil connected to a receiver controller 116. Thus, the receiver coil allows both for data communication with an external control device 200 as well as power reception via inductive power transmission from the external control device 200. As the skilled person will understand, alternatively, a transceiver can be provided being a separate component of the internal electronic unit 110. All of the components are connected to a power management unit 107 for management of the electric power necessary for applying the voltages and for the further electronic functions.

The internal electronic unit 110 can communicate with the external control device 200 either directly via cable 215 or through transceiver 115 wirelessly connected to a transmitter which in the shown example is a transmitter coil 217 of the external control device 200 connected to a corresponding transmitter controller 218. Also both connections can be provided as desired. The external control device receives electric power from an external power source 400 which is fed to a power controller 207. Using a transmitter controller 219, electric power can be fed from the external control device 200 to the internal electronic unit 110 either wirelessly via inductive power transmission through transmitter 217 and transceiver 115 or through cable 215. In turn, the external control device 200 can receive signals from the sensors 123, 125 which can be displayed using a screen 231 connected to a corresponding controller 230. The parameters can thus be read by a human operator, i.e. for example by a doctor who can interact with the external control device 200 making use for example of a keyboard 233. Using the keyboard, the operator can control functions of the internal electronic unit 110, for example can control the voltages applied through the electrodes 111, 113 and 114. Similarly, the system can provide for an automized feedback loop, i.e. in response to sensor signals transmitted by the internal electronic unit 110 to the external control device 200, the external control device can automatically respond by controlling the voltages applied through electrodes 111, 113 and 114.

Figure 3:
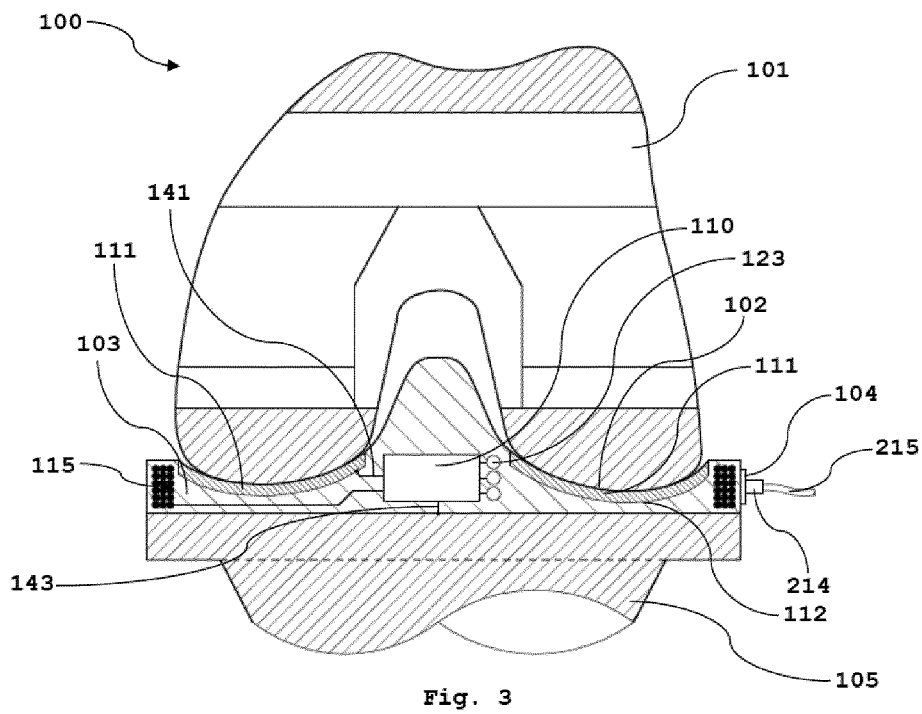
FIG. 3 shows a schematic cross-sectional view of the artificial knee.

FIG. 3 shows a cross-sectional view of the artificial knee 100. As shown, the internal electronic unit 110 is provided within the intermediate portion 103. The internal electronic unit 110 is electrically connected to a first electrode 111 via an electrical connection 141 (only one shown in the figure). As can be taken from this figure, the first electrode 111 is attached to an outer surface 112 of the intermediate portion 103 and is arranged essentially parallel to said outer surface, i.e. both surfaces are curved in the same way. This electrode is arranged in between the intermediate portion 103 and the first joint portion 101 and is in electrical contact with a corresponding contact surface 102 of the first joint portion 101. In this way, movement of the first joint portion 101 with respect to the second joint portion 105 is still possible. In other words, the first joint portion, i.e. the femoral portion of the artificial knee can be pivoted with respect to the tibial portion 105.

The internal electronic unit 110 is further provided with sensors out of which only sensor 123 is labeled in the figure. As the skilled person will take from the figure, the sensors are provided at the internal electronic unit 110 being in contact with the environment of the artificial joint such as with the synovial fluid in order to detect parameters such as e.g. temperature of the synovial fluid, pH of the synovial fluid, and/or conductivity of the synovial fluid or the like.

The internal electronic unit 110 is further electrically connected with the tibial portion 105 via electrical connection 143. In the figure a coil 115 is shown in a cross-sectional view which is a receiver coil for example for the reception of power via inductive power transmission from the external control device 200. As shown, the coil 115 is embedded within the intermediate portion 103 and thus advantageously secured against influences for example from synovial fluid surrounding the artificial knee.

The artificial knee is further provided with a socket 104 within the intermediate portion 103 which in the figure has received a plug 214 connected to a cable 215 for communication with the external control device 200.

Figure 4:
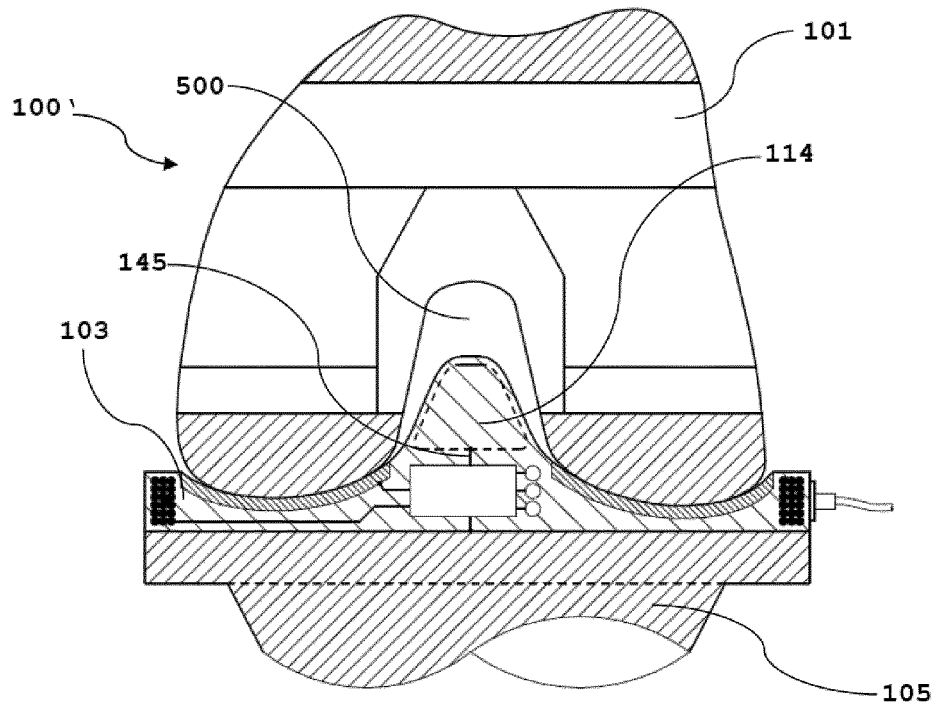
FIG. 4 shows a schematic cross-section of a further embodiment of the artificial joint.

FIG. 4 illustrates a further embodiment of the artificial joint 100'. As compared to the embodiment of the artificial joint 100 shown in FIG. 3, the artificial joint 100' is provided with a central electrode 114 connected to the internal electronic unit 110 via electrical connection 145. As shown, the central electrode 114 is provided within an outer surface of the intermediate portion. The dashed lines indicate indicates that the electrode is located behind the section illustrated by the two-dimensional cross-sectional view. The central electrode 114 thus is in electrical contact with synovial fluid which may be present within cavity 500.

Figure 5:
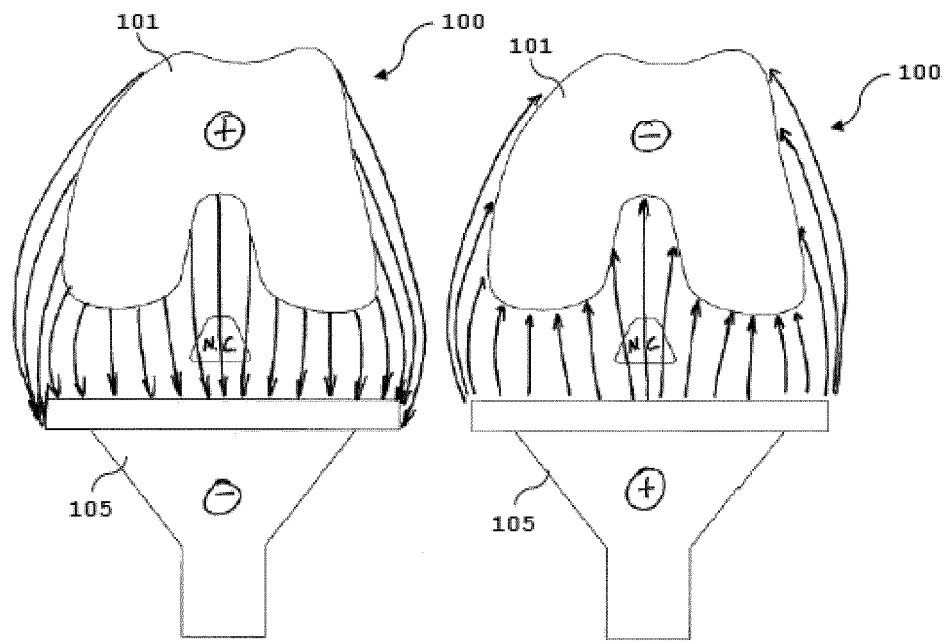
FIG. 5 illustrates an electric field distribution for an artificial joint.
Figure 6:
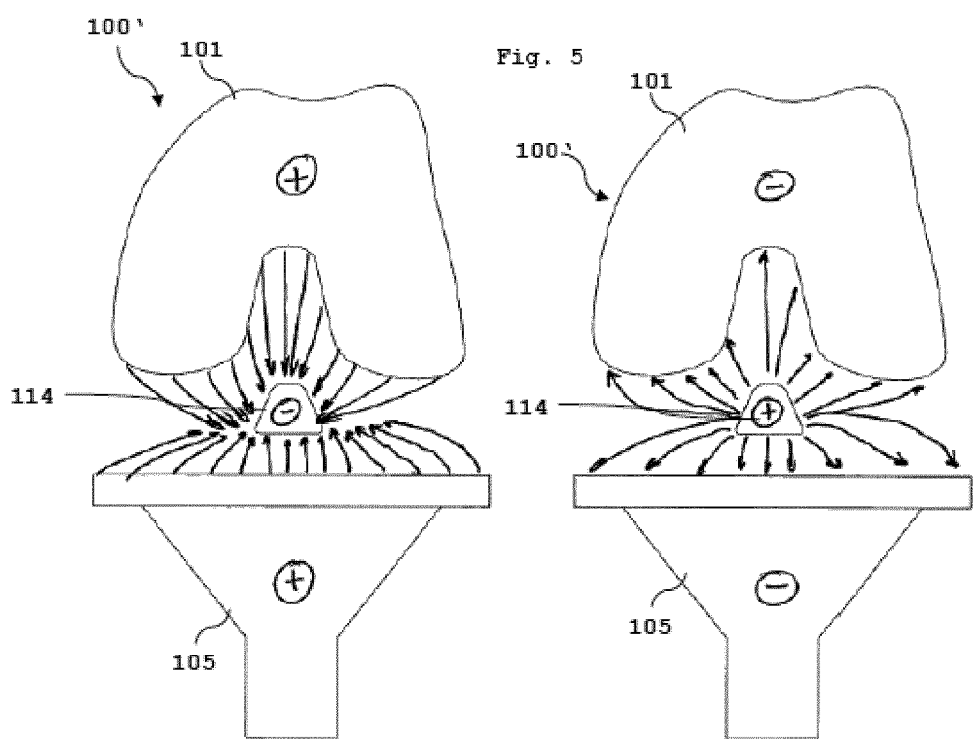
FIG. 6 shows the electric field distribution for a further embodiment of the artificial joint.

FIGS. 5 and 6 illustrate possible electrical field distributions. As shown in FIG. 5, by connecting a positive voltage to the femoral portion 101 and a negative voltage to the tibial portion 105, the electrical field as illustrated by the arrows in the left part of FIG. 5 is orientated essentially pointing from the femoral portion 101 to the tibial portion 105. As shown in the right part of FIG. 5, by setting the tibial portion to a positive polarity, and the femoral portion to a negative polarity, the electrical field as indicated by the arrows is essentially orientated from the tibial portion towards the femoral portion. In both cases as shown in FIG. 5, the central electrode is not used.

If it is desired to fine-tune the electrical field distribution, or even change the field distribution, the central electrode 114 can be applied as illustrated in FIG. 6. As shown, setting both the femoral and the tibial portion to a positive polarity, and the central electrode 114 to a negative polarity, the electrical field, as illustrated by the arrows in the left part of FIG. 6, points from the tibial portion and the femoral portion to the central electrode 114. In the opposing case in which the tibial portion and the femoral portion are set to a negative polarity and the central electrode 114 is set to a positive polarity, the electric field as illustrated by the arrows points from the central electrode 114 towards the tibial and the femoral portions.

As it will be clear for the person skilled in the art, in addition to these cases where the central electrode 114 is set to a polarity different from both the tibial portion and the femoral portion, it is also possible to set the central electrode 114 and one of the tibial or femoral portion to the same polarity which is different from the polarity of the other of the femoral or the tibial portion. Thus, even though by applying voltages to the first joint portion 101 and to the second joint portion 105, a global electrical field pointing from one of these portions to the other of these portions, can be achieved which is sufficient for achieving a repelling effect preventing adhesion of bacteria to the joint surfaces, the central electrode 114 allows for a plurality of field distributions. Thereby, it becomes possible to fine-tune the electrical field distribution, e.g. in accordance with geometrical requirements of the artificial joint in question.

Figure 7:
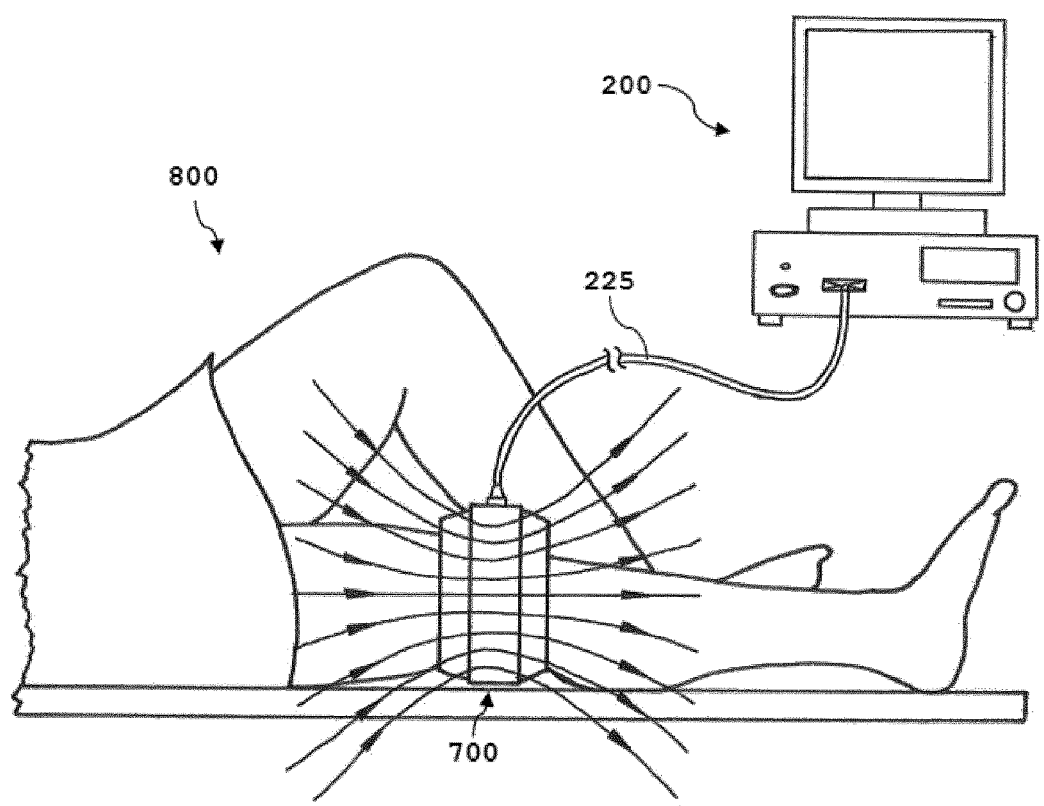
FIG. 7 illustrates a knee pad connected to an external control device housing a transmitter coil.

FIG. 7 illustrates a system comprising the artificial joint 100 (not visible in the figure) and the external control device 200. In the shown embodiment, the transmitter coil (not visible in the figure) is provided outside of the external control device 200 connected therewith through an electrical connection 225. The transmitter coil is provided within a knee pad 700 attached to the knee of a patient 800 around the artificial joint 100. As indicated by the curved arrows in the figure, the transmitter coil generates magnetic fields through which the transmitter coil can communicate with the receiver coil (not visible in the figure) forming the transceiver of the internal electronic unit (not visible in the figure). Thus, it is possible that the external control device 200 feeds electrical power to the artificial joint 100 via inductive power transmission while at the same time, data communication between the internal electronic unit and the external control device is enabled. In other words, for example signals from sensors connected to the internal electronic unit can be communicated to the external control device 200 while the external control device 200 can communicate control signals to the internal electronic unit to control e.g. application of voltages or can control sensors.

The invention claimed is:

1. An artificial joint comprising a first joint portion, a second joint portion and an intermediate portion which are mechanically connected such that the first joint portion is movable with respect to the second joint portion; wherein
the first joint portion and the second joint portion each comprise an electrically conductive material and the intermediate portion comprises a non-conductive material and is arranged in between the first joint portion and the second joint portion such that the first joint portion is electrically isolated from the second joint portion;
wherein:
the artificial joint further comprises an internal electronic unit which is provided inside of the intermediate portion and is connected to the first joint portion via at least one first electrode and to the second joint portion via at least one second electrode such that a first electrical voltage can be applied to the first joint portion and a second electric voltage can be applied to the second joint portion, whereby the first electrical voltage and the second electrical voltage are applied with reference to a common reference potential.

2. The artificial joint according to claim 1, wherein the first electrode is attached to an outer surface of the intermediate portion, arranged essentially parallel to said outer surface in between the intermediate portion and the first joint portion in electrical contact with a corresponding contact surface of the first joint portion, thus electrically connecting the first joint portion and the internal electronic unit inside of the intermediate portion.

3. The artificial joint according to claim 1, wherein the artificial joint further comprises a central electrode provided in between the first joint portion and the second joint portion, whereby the internal electronic unit is adapted to apply a third electrical voltage to the central electrode, whereby the third electrical voltage is applied with reference to the common reference potential.

4. The artificial joint according to claim 1, wherein the central electrode is provided within an outer surface of the intermediate portion in electrical contact with synovial fluid.

5. The artificial joint according to claim 1, wherein the first and second electrical voltages are applied such that the first joint portion and the second joint portion are set to the same polarity and the third electrical voltage is applied such that the central electrode is set to the opposing polarity.

6. The artificial joint according to claim 1, wherein the internal electronic unit is adapted to communicate with an external control device, the external control devices thus being adapted to control an application of the first electrical voltage and the second electrical voltage, preferably and the third electrical voltage.

7. The artificial joint according to claim 1, wherein the internal electronic unit is adapted to apply the first and the second electrical voltage such that a resulting electrical field strength is between 0 V/cm and 60 V/cm.

8. The artificial joint according to claim 1, wherein the first electrical voltage is applied to the first joint portion and the second electrical voltage is applied to the second joint portion, the first joint portion and the second joint portion are charged accordingly and a resulting electrical field is generally oriented from one of the first joint portion and the second joint portion to the other one of the first joint portion and the second joint portion.

9. The artificial joint according to claim 1, wherein the internal electronic unit is further provided with a transceiver and the external control device is provided with a transmitter such that the external control device is adapted to wirelessly control an application of the first electrical voltage and the second electrical voltage.

10. The artificial joint according to claim 1, wherein the artificial knee further comprises a transceiver coil provided within the intermediate portion in electrical connection with the internal electronic unit, and the external control device is provided with a transmitter coil such that electrical power necessary for applying the voltages can be provided from the external control device to the internal electronic unit through the transceiver coil and the transmitter coil by inductive power transmission.

11. The artificial joint according to claim 1, wherein the transceiver coil is provided embedded within an outer portion of the intermediate portion surrounding the internal electronic unit.

12. The artificial joint according to claim 1, wherein the internal electronic unit is further provided with at least one sensor which is provided in communication with the environment of the artificial joint and thus adapted to detect at least one of temperature of the synovial fluid, conductivity of the synovial fluid, pH of the synovial fluid or a marker of cell death within the synovial fluid.

13. The artificial joint according to claim 1, wherein the internal electronic unit is adapted to communicate a signal received from the at least one sensor to the external control device and the external control device is adapted to automatically adjust the first electrical voltage applied to the first conductive component and the second electrical voltage applied to the second conductive component in response to the sensor signal.

14. The artificial joint according to claim 1, wherein the artificial joint is a knee prosthesis, the first joint portion is a femoral portion, the second joint portion is a tibial portion and the intermediate portion is a polyethylene insert provided in between the femoral portion and the tibial portion.

15. A system comprising the artificial joint according to claim 1 and an external control device adapted to control an application of the first electrical voltage and the second electrical voltage.

16. The artificial joint of claim 6, wherein the internal electronic unit is adapted to communicate with an external control device, the external control device thus being adapted to control an application of the first electrical voltage, the second electrical voltage, and the third electrical voltage.

17. The artificial joint of claim 7, wherein the internal electronic unit is adapted to apply the first and the second electrical voltage such that a resulting electrical field strength is between 0 V/cm and 55 V/cm.

18. The artificial joint of claim 7, wherein the internal electronic unit is adapted to apply the first and the second electrical voltage such that a resulting electrical field strength is between 0 V/cm and 40 V/cm.

19. The artificial joint of claim 7, wherein the internal electronic unit is adapted to apply the first and the second electrical voltage such that a resulting electrical field strength is between 0 V/cm and 20 V/cm.

20. The artificial joint of claim 7, wherein the internal electronic unit is adapted to apply the first and the second electrical voltage such that a resulting electrical field strength is between 10 V/cm and 20 V/cm.

* * * * *